United States Patent [19]

Loeser

[11] 4,187,847
[45] Feb. 12, 1980

[54] AIRLESS INTRAVENOUS FLUID SYSTEM

[76] Inventor: Edward A. Loeser, 8646 Oak Valley Dr., Sandy, Utah 84070

[21] Appl. No.: 814,185

[22] Filed: Jul. 11, 1977

[51] Int. Cl.² .............................................. A61M 5/00
[52] U.S. Cl. ................................... 128/214 F; 73/229; 128/DIG. 12; 222/103
[58] Field of Search ........... 128/214 R, 214 E, 214 F, 128/214.2, 226, DIG. 12; 222/103; 73/229; 116/117 C

[56] References Cited

U.S. PATENT DOCUMENTS

| 1,793,077 | 2/1931 | Frick | 222/103 |
|---|---|---|---|
| 3,595,232 | 7/1971 | Leibinsohn | 128/214 F |
| 3,636,767 | 1/1972 | Duffy | 73/229 |
| 3,640,277 | 2/1972 | Adelberg | 128/214 F |
| 3,780,732 | 12/1973 | Leibinsohn | 128/214 F |
| 3,832,998 | 9/1974 | Gregg | 128/214 E |
| 4,090,514 | 5/1978 | Hinck et al. | 128/214 F |

FOREIGN PATENT DOCUMENTS 2053995  5/1972  Fed. Rep. of Germany ....... 128/214 F Primary Examiner—Dalton L. Truluck
Attorney, Agent, or Firm—Trask & Britt

[57] ABSTRACT

An intravenous fluid therapy system includes a source of intravenous fluid which is an intravenous-fluid-filled non-vented container having deformable side walls. Pressure means substantially surrounds the side walls of the source to pressurize the intravenous fluid therein. The pressure means includes tensioning means to cause the pressure means to exert a force against the side walls. An airless flow meter receives intravenous fluid from the source by a tube means. The airless flow meter includes flow indication means which may be a plurality of fins symmetrically secured to a hub rotatably mounted within a non-vented chamber. An outlet from the flow meter is connected by tube means to an intravenous catheter. In operation, the source is pressurized to allow intravenous fluid to flow through the tube means and the airless flow meter and out the catheter to urge all air therefrom. The pressure means maintains a fluid head to force the fluid from the source through to the catheter means without venting during intravenous fluid administration.

3 Claims, 11 Drawing Figures

AIRLESS INTRAVENOUS FLUID SYSTEM

BACKGROUND OF THE INVENTION

1. Field

This invention relates to intravenous fluid therapy systems. More particularly, this invention provides an intravenous fluid therapy system to provide intravenous fluid under pressure without exposure or contact of the intravenous fluid to the atmosphere.

2. State of the Art

Intravenous (IV) therapy systems are well known. In general, they include a fluid supply and a catheter apparatus within interconnecting tubing. A metering device such as a drip chamber may be provided in the interconnecting tubing to permit adjustment of the intravenous fluid flow rate and in turn the injection rate into the vein (or vessel) of a patient. In particular, a catheter apparatus which is frequently of the type comprised of a stylet in a cannula attached to a hub is inserted into a patient's vein (or vessel). After insertion, the stylet is removed and intravenous system tubing is connected to the hub. The tubing is in turn connected to a fluid supply which may be a bottle or bag of intravenous fluid suspended at a height above the intravenous therapy site so that a fluid head in excess of blood pressure is available to cause fluid flow. The source of IV fluid is frequently vented to the atmosphere. The atmosphere generally contains a wide variety of microscopic or otherwise small particulate matter which may in many circumstances be detrimental if injected into a patient's blood stream. By venting an IV fluid system to the atmosphere, there exists a distinct possibility that undesirable organisms or matter may become suspended or dissolved in the intravenous fluid and thereby be injected into the blood system of a patient. Further, a drip chamber is typically vented so that fluid literally drips through a chamber vented to the atmosphere. The drip rate (number of drops per unit time) is frequently used as an indicia of IV therapy flow rate and administration rate (milliliters per unit time). Accordingly, IV fluid may be exposed to the atmosphere both through the source (bottle) which may be vented to the atmosphere and through a drip chamber. Also, some spillage has occurred with the use of vented bottles.

In a hospital, frequently the atmosphere can be more hazardous than ordinary atmosphere. That is, in selected circumstances, one may find a variety of contagious organisms or hazardous matter. Because of the increased and wide use of antibiotics in medical treatment, and in particular in hospitals, it is generally known that a variety of antibiotic-resistant organisms may become airborne to expose patients to what has been termed "staph" infection or similar maladies. A vented inrtraveous therapy system is particularly susceptible to becoming a vehicle which communicates these airborne organisms into a patient.

In any vented intravenous fluid system, it is distinctly possible that air may be entrained in the tubing and thereafter injected into the patient. Injection of air into a blood vessel can have fatal consequences.

Also, IV therapy in environments where atmospheric pressure is varying or abnormal or where gravity is not reliable (e.g., airborne, space, decompression chamber) is difficult because of problems in flow rate and the risks of dissolved gases going into or coming out of solution. A sealed or airless system is desirable for such applications.

SUMMARY OF THE INVENTION

An intravenous fluid therapy system is provided which includes a non-vented source of intravenous fluid, pressure means adapted to the source to pressurize the intravenous fluid, an airless flow meter, catheter means and tube means interconnecting the source to the flow meter and the flow meter to the catheter. The source is preferably an intravenous-fluid-filled non-vented container having deformable side walls.

In one embodiment, the pressure means includes two spaced apart members for positioning adjacent the side walls and tensioning means adapted to the surface members to cause the surface members to exert a force against the side walls. In turn, a pressure or fluid head is generated to overcome blood pressure and to force the fluid through the interconnecting tubing and the flow meter into the vein (vessel) of a patient. The surface members may have edges and a plurality of attachment means affixed thereto along the edges. The tensioning means may include an elastic member removably positioned about and secured to selected attachment means in a pattern to tension the surface members together. The surface members may be hingedly secured to each other along one edge thereof and may be sized approximately the size of the source side walls.

In another embodiment, the surface members are assembled into an upper pair and lower pair each hingedly secured to each other along first edges. Suspension means is adopted to the upper pair along the first edge. An aperture is formed in the lower pair along its first edges. The upper pair is positioned about the upper part of the container; and the lower pair is positioned about the lower part of the container with its mouth in the aperture. Tensioning means extend between second edges of the lower pair members and the upper pair members.

In a preferred embodiment, the pressure means may be a piece of elastic material sized to substantially surround the container. The material has securing means to secure the material about the container to exert a force against the side walls of the container. The securing means may include a plurality of first attachment means interspaced along a first transverse edge of the material and second attachment means to coact with the first attachment means. The second attachment means may be positioned in a series of spaced apart transverse rows from a second transverse edge of the material.

The airless flow meter may be comprised of an inlet connection means for connecting the flow meter to the tube means to receive fluid from the source. The chamber may be connected to receive fluid from the inlet connection means. The chamber has no vent and has flow indication means positioned therein. The flow meter also has an outlet connection means connected to receive fluid from the chamber and to connect the tube means to supply fluid to said catheter. The flow indication means may be a plurality of fins symmetrically secured to a hub rotatably mounted within the chamber. The fluid preferably flows from the inlet to the outlet connection means in a manner to impinge on said fins to cause said fins to rotate at a rate related to the flow rate of the fluid.

A method of intravenous therapy is also disclosed wherein a source of intravenous fluid is pressurized with pressure means to supply fluid under pressure through an airless flow meter and interconnecting tubing through a catheter means which is inserted into the vein or vessel of a patient. Prior to inserting the catheter into the vein of the patient the tubing and flow meter and catheter are purged of air by applying pressure and allowing intravenous fluid to flow therethrough.

BRIEF DESCRIPTION OF THE DRAWINGS

In the drawings, which illustrate the best mode presently contemplated for carrying out the invention.

DESCRIPTION OF THE ILLUSTRATED EMBODIMENT

Figure 1:
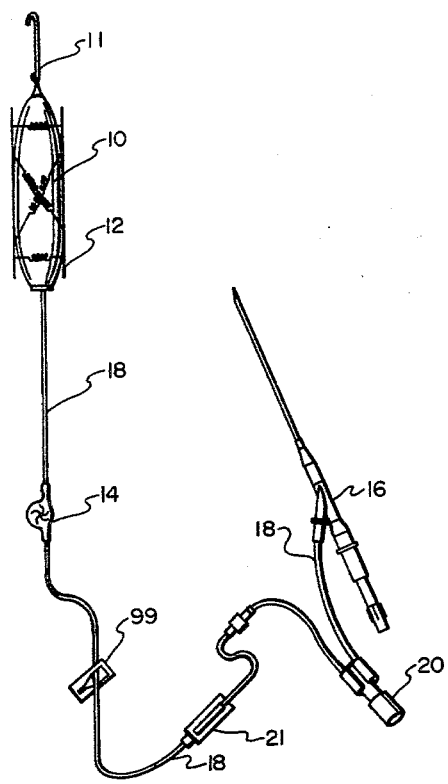
FIG. 1 is a perspective side view of an intravenous fluid therapy system of the instant invention.

The intravenous fluid therapy system of the instant invention includes a source of intravenous fluid 10, pressure means 12, an airless flow meter 14, a catheter 16, and interconnecting tubing 18. The pressure means 12 exerts a pressure on the source 10 to cause intravenous fluid therein contained to flow therefrom through the flow meter 14 and interconnecting tubing 18 to the catheter 16, which in operation is inserted into the vein or vessel of a patient for purposes of intravenous fluid therapy. As shown in FIG. 1, a non-kink device 20, such as that described and disclosed in U.S. Pat. No. 3,942,528 (Loeser), is included in the tubing 18. However, it is not essential to the invention and is a preferable device to be included therein for the convenience of the user. Similarly, an air eliminator and filter 21, such as that disclosed in U.S. Pat. No. 3,803,810, may be used if desired.

Figure 7:
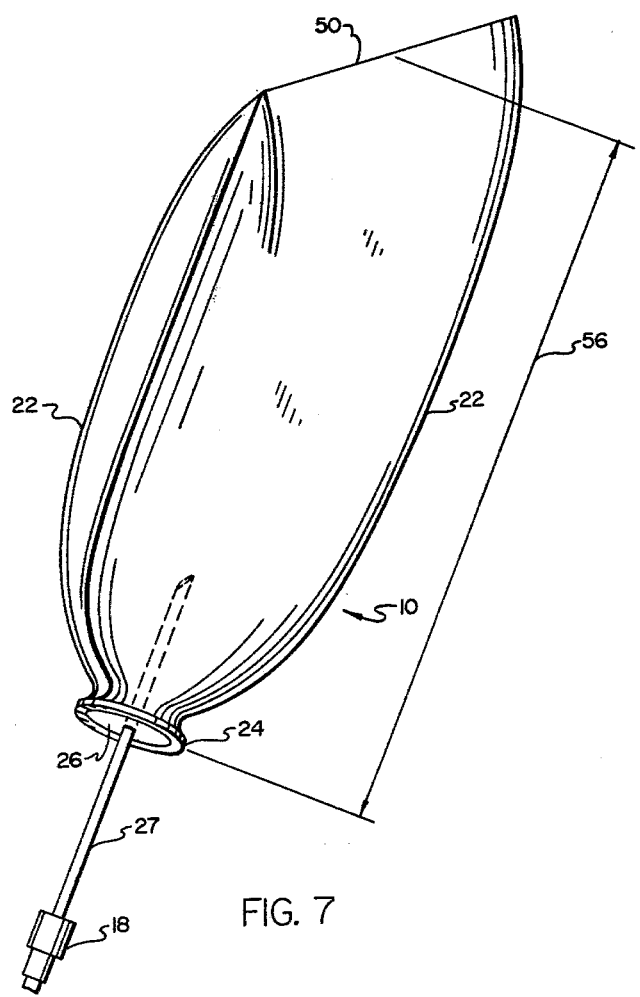
FIG. 7 is a perspective view of an intravenous fluid source for use within the intravenous fluid therapy system of the instant invention.

The intravenous fluid source 10 is best shown in FIG. 7 as a bottle-like structure having deformable side walls 22. The source has a mouth 24 which has a seal 26. It may be noted that the seal 26 and in turn the source 10 has no provision for venting the source 10 to the atmosphere. The pressure means 12, such as that disclosed in FIGS. 2 through 5, surrounds the source 10 and supplies a force against the side walls 22 to in effect squeeze the fluid therefrom through the mouth 24 via a connection 27 here shown to be a sharpened insert. Other connectors 27 may be used which are known to those skilled in the art.

Figure 2:
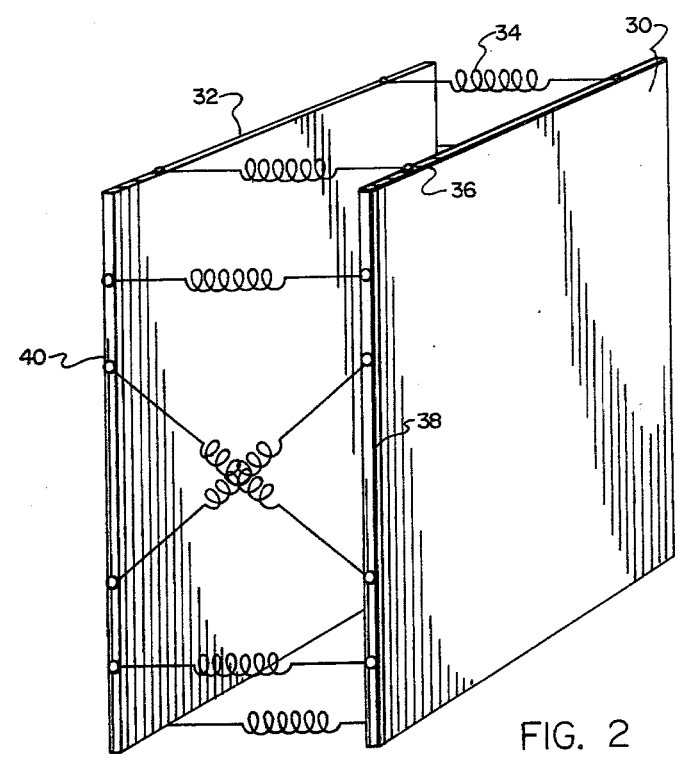
FIG. 2 is a perspective view of the pressure means of an intravenous fluid therapy system of the instant invention.

Referring now to FIG. 2, a pressure means 12 includes opposite side walls 30 and 32 which are substantially rectalinear in shape to conform substantially to the rectalinear projection of the side walls 22 of the source 10 as shown in FIG. 7. The pressure means 12 is positioned about the deformable side walls 22 as best shown in FIG. 1. Tensioning means 34, which as shown in FIG. 2, are spring-like devices which may be in fact metal springs, rubber bands, elastics or other devices which may tension or tend to pull the opposite members 30 and 32 of the pressure means together against the side walls 22 of the source 10. A variety of tensioning means 34 in selected patterns are desirable to provide, in effect, a fairly uniform tensioning of the two members 30 and 32 together. The members 30 and 32 have pins 36 or other securing means positioned along the edges 38 and 40 thereof to receive the tensioning means 34 in the selected pattern.

Figure 3:
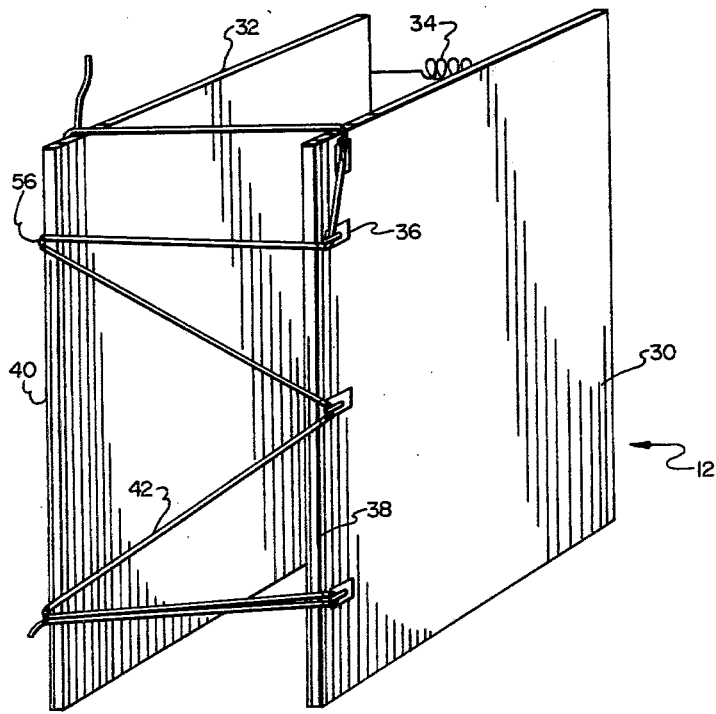
FIG. 3 is a perspective view of alternate pressure means for an intravenous therapy system of the instant invention.
Figure 4:
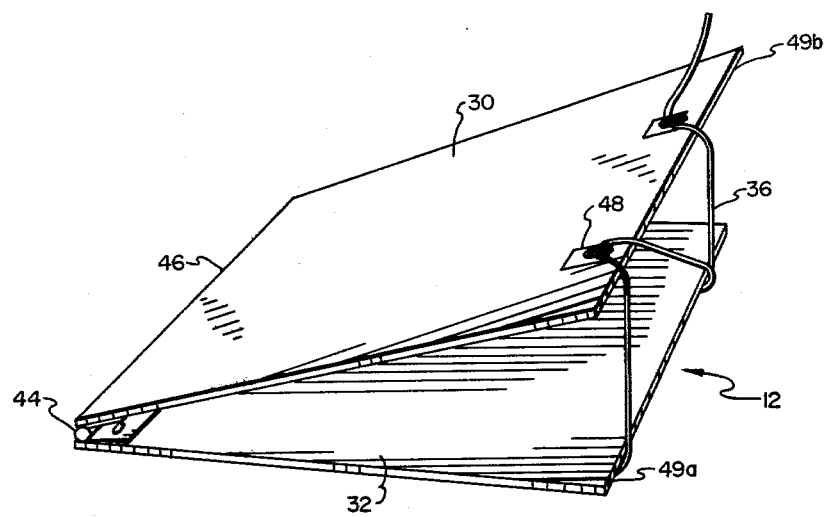
FIG. 4 is a perspective view of alternate pressure means for the intravenous fluid therapy system of the instant invention.

As shown in FIG. 3, the tensioning means may include a rubber band or elastic 42 which may be wound in a preselected pattern about the various pins 36 positioned along the edges 38 and 40 of the members 30 and 32. FIG. 4 illustrates pressure means hingedly secured by a crease or hinge 44 along one edge 46 of the members 30 and 32. The tensioning means 36 may be simply affixed in a tensioning manner between selected pins or hooks 48 along the opposite edges 49a and 49b. As envisioned for the embodiment of FIG. 4, the upper edge 50 of the source 10 (FIG. 7) would be positioned proximate the hinged end or edges 46 of the pressure means of FIG. 4. The mouth 24 would extend away from the opposite edges 49a and 49b.

Figure 5:
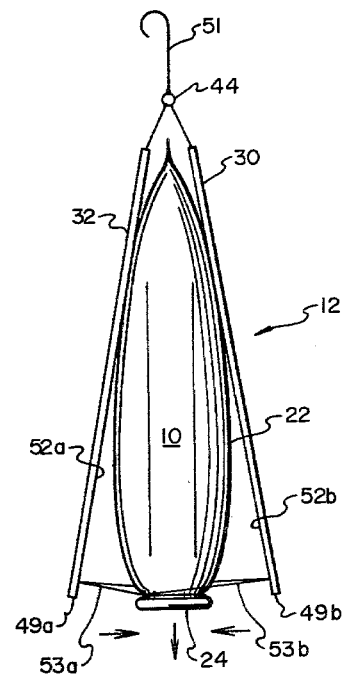
FIG. 5 is a side view of alternate pressure means for the intravenous fluid therapy system of the instant invention.

The apparatus of FIG. 4 need not be suspended at a height above the intravenous site. However, it may be adapted for suspension as shown in FIG. 5. A hook or other suspension means 51 is adapted to the hinge 44. The inner surfaces 52a and 52b of the side members 32 and 30 are formed to be convex as to the source surfaces 22. The source 10 is secured to the pressure means 12 by removable elastic bands 53a and 53b positioned tensionally around the mouth 27 of the source 10. The tension of the bands 53a and 53b, coupled ith the gravitational force, pull the members 32 and 30 against the surfaces 22 to pressurize the fluid therein.

Figure 6:
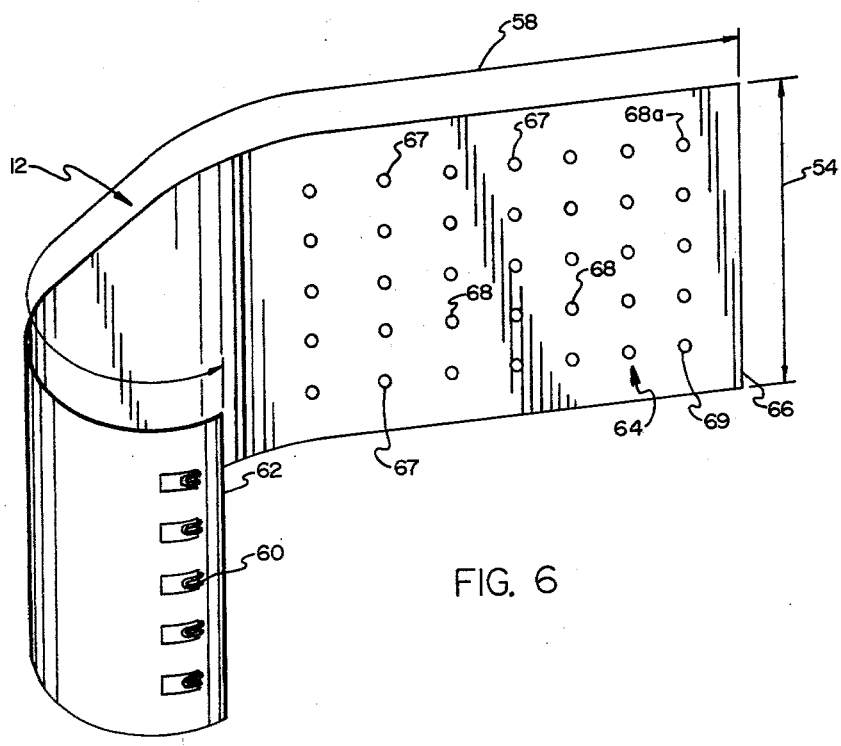
FIG. 6 is a perspective view of alternate pressure means for the intravenous fluid therapy system of the instant invention.

Referring now to FIG. 6, an alternate pressure means 12 is illustrated. It is a piece or section of elastic-like material or cloth. That is, the material has an elastic characteristic to exert a force to return it to a normal unstretched condition from a stretched condition. As known to those skilled in the art, it may be made out of a plurality of elastic or rubber-like fibers giving the material the characteristic as above described. The material is generally sized in width 54 to be roughly the height 56 (FIG. 7) of the source 10. The material is sized in length 58 to surround the source 10. The material has a first attachment means 60 positioned along a first transverse edge 62. A second attachment means 64 is positioned along a second transverse edge 66. The first attachment means, as here illustrated, is comprised of a plurality of hooks in spaced relationship along the edge 62. The second attachment means 64 is comprised of a plurality of transverse rows 67 of holes 68 positioned in spaced relationship with respect to each other in each of the rows 68. Thus, as the material is first wrapped about the source 10 it may be connected along the first row 69. As the fluid leaves the source 10 and the size of the source 10 thereby decreases, it may be necessary to tighten the material about the source 10 by stretching the material to a second or third or fourth row of holes as necessary to maintain the pressure. Of course, upon installation with a full source 10, it may te desirable to stretch a material as tightly as reasonably feasible about the source to minimize the need for adjustments as the fluid is expelled and the source 10 depletes. It is anticipated that with the flow rate of a few milliliters per hour, it may be a lengthy period (e.g., several hours) before the source 10 depletes sufficiently to cause or to require a tightening of the material. In view of the fact that attending personnel frequently observe a patient receiving intravenous fluid therapy, adjustment by tensioning in this manner is not regarded as inefficient.

It may also be noted that by pressurizing the source 10 with pressure means 12, such as those herein illustrated, it is not necessary to elevate the source of intravenous fluid above the patient to create a pressure head to cause the intravenous fluid to flow through the tubing drip chamber into the vein of a patient as may be conventionally required.. Thus, in emergency situation, paramedics or other attending personnel attending to a patient in a non-hospital environment, may not be required to hold the intravenous fluid source in an elevated position above the patient while administering or otherwise attending to the patient in what may be regarded as an extremely difficult environment at or near the scene of trauma or wherever the patient may be found.

Figure 8:
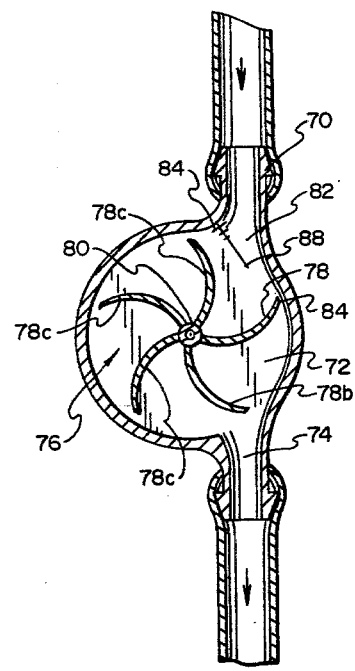
FIG. 8 is a sectional side view of an airless flow meter for use with the intravenous fluid therapy system of the instant invention.

Referring now to FIG. 8, an airless flow meter 14 is shown having a first connector 70 to receive intravenous flui from the source 10, a chamber 72 and a second connector 74 to supply fluid to the catheter 16. The chamber 72 has means to indicate the flow of intravenous fluid therethrough. As here shown, such means is a pinwheel or rotor 76 comprised of a plurality of fins 78 connected to a hub 80 which is rotatably mounted within the chamber 72. The chamber 72 is connected to receive the intravenous fluid from the first connector means 70 and supply the intravenous fluid to the second connector means 74. As shown, the chamber 72 may have a flow direction port 82 on its inlet side in order to direct the fluid passing therethrough towards the outer end of the fins 78 in order to provide the maximum torque to cause the pinwheel 76 to rotate. It may also be noted that the fins 78 are arcuate in shape to reduce the drag of the fins 78 as they pass through fluid as they rotate and to improve the transference of torque thereto from the intravenous fluid. It may be noted that the chamber 72, as here shown, has no vent to the atmosphere. It does have an aperture 84 formed near the port 82 to prevent air and other gases from collecting in the chamber 72. In operation, the flow rate is substantially proportional to the revolution rate (i.e., rpm) of the pinwheel 76. Individual fins 78b, 78c, 78d and 78e may be colored differently (e.g., red, white, black, green, yellow) so that when observing one can determine the number of fins that pass a scribe or other well defined structure, such as the throat 88, within a prescribed or selected period of time. An appropriate chart may be empirically developed to list predetermined flow rates for the various rpm figures obtained by observation.

Figure 9:
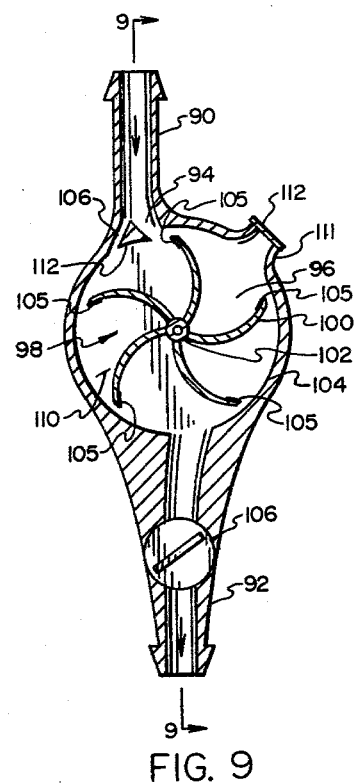
FIG. 9 is a side view of an airless flow meter for use with an intravenous fluid therapy system of the instant invention.
Figure 10:
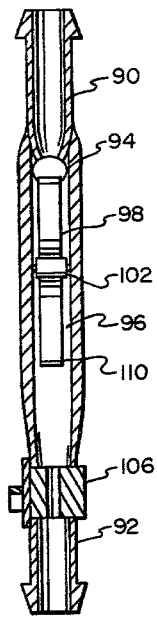
FIG. 10 is a cross-sectional view of the airless flow meter illustrated in FIG. 8 along section lines 9—9.

Referring now to FIGS. 9 and 10, an alternate flow meter is shown which also has inlet connection means 90 and outlet connection means 92. The fluid flows from the first connection means 90 through a throat 94 into the chamber 96 to rotate the pinwheel 98 rotatably positioned therein. The pinwheel, as here indicated, is comprised of a plurality of fins 100 adapted to a hub 102 which is rotatably mounted within the chamber 96. As shown in FIG. 10, the inlet and outlet connetors 90 and 92 are displaced or positioned with respect to the chamber so that the fluid flowing therethrough must travel a greater distance along the inner perimeter 104 of the chamber 96. In so doing there is a more continuous integrated torque available to rotate the pinwheel 98. The fins 100 may be of different color as the fins 78 for the flow meter of FIG. 7. One or all fins may have a magnet 105 or magnetized material positioned thereon so that means may be cooperatively associated therewith to read flow rate electronically and transmit the flow rate data to a remote location in, for example, an intensive care environment. It may be also noted, that a vlave or plug cock 106 is positioned in the outlet connection means 92. The plug cock 106 may be used to regulate the flow rate of the IV fluid through the flow meter and in turn into the patient. The flow meter shown also is not vented to the atmospher. Rather, it has a vent 107 through the throat 94 to facilitate purging and prevent gas collection. A port 111 with a removable cap 112 may be provided to collect gas and allow for manual venting of the flow meter when desired.

The flow meter of FIGS. 9 and 10, as well as the flow meter of FIG. 8, may be constructed of a variety of different materials. However, it is most preferred that the material surrounding the chamber 72 (FIG. 8) and 96 (FIGS. 9 and 10) be translucent so that an observer may observe the rotation rate of the pinwheels 76 and 98. Preferably, the entire flow meter may be formed as two matching symmetric halves and assembled with the pinwheel being positioned therein.

Figure 11:
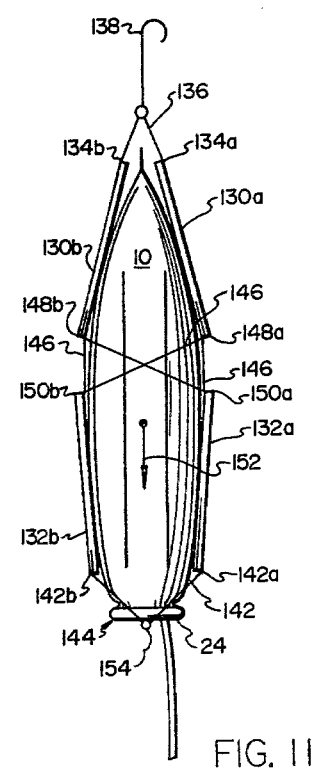
FIG. 11 is a side view of alternate pressure means of an intravenous fluid therapy system of the instant invention.

FIG. 11 illustrates an alternate pressure means comprised of an upper pair of surface members 130a and 130b and a lower pair of surface members 132z and 132b. The upper pair 130 are secured to each other along a first edge 134a and 134b with a hinge 136. Suspension means, here shown as a hook 138, is affixed to the hinge 136 to allow the user to suspend the device from a conventional intravenous suspension apparatus. The lower pair 132 are secured to each other along first edges 140a and 140b by a hinge 142. An aperture 144 is formed in the hinge 142 to receive the mouth 24 of the container 10. Tensioning means 146, which may be elastic or rubber bands, extend between the second edges 148a, 148b, 150a and 150b of the upper and lower pairs 130 and 132. As shown, the second edges 148 and 150 are opposite the first edges 134 and 142. In operation, the weight of the fluid in the container 10 generates a downward force shown by the arrow 152 when the device is suspended by the hook 138. The force 152 will be resisted at the axis 154 of the hinge 142 so that the upper and lower pairs 130 and 132 will tend to squeeze against the container by force resolution and by the force exerted by the tensioning means 146.

In operation, it is preferred that a catheter 16 be of the type which permits preconnection prior to venapuncture. That is, the catheter 16 should be of the type which allows the intravenous tubing 18 to be preconnected so that it may be purged prior to inserting the stylet and catheter into the vein of a patient and so that thereafter the stylet may be removed without having to connect or re-connect the IV tubing 18. An ANGI- OCATH with Y adapter manufactured by Deseret Pharmaceutical Corporation of Sandy, Utah, is one such device. It must be noted however, that it is preferred, but not required, that such a catheter be used.

In a hospital or a comparable treatment facility, the pressure means 12 is assembled or positioned about the source 10. The source 10 with the pressure means 12 may be suspended from appropriate structure by a hook 11 or other means as available (FIG. 1). Thereafter intravenous tubing 18, which is frequently prepackaged in a sterile container, is connected through the membrane 26 at the mouth 24 of the source 10. The tubing 18 is thereafter connected to the flow meter 14 and a non-kink device 20 as hereinbefore described. A simple tubing clamp 99 (FIG. 1) may be used to prohibit immediate fluid flow through the tubing 18. The clamp 99 may be also used, as is known to those skilled in the art, to regulate fluid flow through the tubing 18. A filter to remove air 21 (FIG. 1) may also be used.

The absence of air and non-reliance on air pressure is important in situations where therapy is required in environments not having standard atmospheric conditions. Changing atmospheric pressures in airborne, underwater (E.g., hyperbaric or decompression pressure chambers) or space craft preclude the use of vented systems. Further, in such environments, problems of dissolved gases become significant. The instant invention minimizes the hazards of intravenous therapy in such environments.

In use, it is desired that fluid be allowed to flow through the tubing 18 and in particular the flow meter 14 to purge all air and gas therefrom. An appropriate receptacle may be used to receive the fluid that will be flowing therefrom to avoid spillage. Thereafter the intravenous fluid tubing 18 may be connected to an intravenous catheter hub of an intravenous catheter 16 which has been positioned within the vein (or vessel) of a patient. However, as noted above, it is desired or preferred that an intravenous catheter of the type allowing preconnection of the intravenous tubing be used. Thus, the tubing 18 may be preconnected so that the entire system, including the catheter, can be purged of all air and gas ontained therein. Venapuncture may be then effected and the flow adjusted based on the revolution rate of the pinwheel within the flow meter 14. In the course of adminstration it may be noted that no air is entering or coming in contact with the intravenous fluid as it is being administered. That is, no air is entering the source 10 as fluid leaves therefrom. Further, no air is in contact with the fluid in the flow meter. Thus, the sterile environment of the fluid is maintained from the source to the patient. In turn, the patient's exposure to foreign organisms and the like is reduced and in particular eliminated as to IV therapy with this form of treatment.

If the airless flow meter of FIGS. 9 and 10 is used, the plug cock valve 106 may be used in lieu of the clamp 21 to regulate the flow rate into the patient. The flow rate can be determined by observing the number of fins 78, 100 that pass a scribe 110 on the side of the chamber 96 of the flow meter or as the flow meter fin pass a predetermined point such as the tip or one edge 112 (FIG. 9) within the flow meter 14 structure. By empirical development, the volume per unit time of intravenous fluid may be determined for any revolution rate of the pinwheel 76, 98. Thus, attending personnel may adjust the flow rate by observing the pinwheel 76, 98 rotation in relation to a scribe or other index and adjusting either the clamp 99 (FIG. 1) or the plug cock 106 (FIGS. 9 or 10).

It is to be understood that the embodiments of the invention herein described are merely illustrative of the application of the principles of the invention. Reference herein to the details of the illustrated embodiments is not intended to limit the scope of the claims which themselves recite those features regarded as essential to the invention.

I claim:
1. An intravenous fluid therapy system comprising:
 a non-vented source of intravenous fluid which is an intravenous-fluid-filled container having deformable side walls, an upper part, and a lower part with a mouth;
 pressure means adapted to said source to pressurize said intravenous fluid, said pressure means including: said side walls, said surface members having edges with a plurality of attachment means affixed thereto along said edges and being sized in surface area dimensions proximate the size of the side walls of said container, and
 tensioning means adapted to said surface members to cause said surface members to exert a force against said side walls, said tensioning means being an elastic member which is an elongated rubber strip removably positioned about and secured to selected attachment means in a pattern to tension said surface members together, and wherein
 said spaced apart surface members are comprised of an upper pair of spaced apart surface members hingedly secured to each other along first edges thereof with means secured to said pair at said first edges to suspend said pair, and a lower pair of spaced apart surface members hingedly secured to each other along first edges thereof with an aperture formed along said edges wherein said upper pair of surface members are positioned about the upper part of said source and said lower pair of surface members are positioned about the lower part of said source with its mouth in said aperture and wherein said tensioning means is adapted to extend between the second edges of said upper pair opposite said first edges thereof and the second edges of said lower pair opposite said first edges thereof;
 an airless flow meter to indicate the flow of intravenous fluid comprised of:
 inlet connection means for connection with said tube means to receive said fluid from said source;
 a chamber connected to receive said fluid from said inlet connection means, said chamber having flow indication means positioned therein, which is a plurality of fins symmetrically secured to a hub rotatably mounted within said chamber;
 outlet connection means connected to said chamber for connection to said tube means to receive fluid from said chamber and to supply fluid to said tube means;
 wherein said fluid flows from said inlet to said outlet connection means to impinge on said fins to cause said fins to rotate proportionally to the flow rate of said fluid, said fins having magnetic means adapted thereto;
 catheter means for insertion into the vein of a patent; and tube means to connect said source to said flow meter and said flow meter to said catheter means.
2. The system of claim 1 wherein said surface members are convex as to said side walls.
3. The system of claim 1 wherein said airless flow meter has valve means structurally in stream to regulate fluid flow rate and vent means connected to said chamber operable to purge gas therefrom.

* * * * *